United States Patent [19]

Raleigh et al.

[11] Patent Number: 5,539,136
[45] Date of Patent: Jul. 23, 1996

[54] SILICONE POLYETHER SURFACTANTS SYNTHESIZED USING CARBAMATE LINKAGE

[75] Inventors: William J. Raleigh, Rensselaer; Michael A. Lucarelli, Ballston Spa; Raymond J. Thimineur, Scotia, all of N.Y.

[73] Assignee: General Electric Company, Waterford, N.Y.

[21] Appl. No.: 310,600

[22] Filed: Sep. 22, 1994

Related U.S. Application Data

[62] Division of Ser. No. 934,052, Aug. 21, 1992, abandoned.

[51] Int. Cl.[6] .................................................... C07F 7/10
[52] U.S. Cl. .................................................... 556/420
[58] Field of Search ............................................ 556/420

[56] References Cited

U.S. PATENT DOCUMENTS

| | | |
|---|---|---|
| 3,402,192 | 9/1968 | Haluska . |
| 4,090,987 | 5/1978 | Abstract . |
| 4,218,250 | 8/1980 | Kasprzak . |
| 4,265,878 | 5/1981 | Keil . |
| 4,268,499 | 5/1981 | Keil . |
| 4,311,695 | 1/1982 | Starch . |
| 4,421,656 | 12/1983 | Donatelli et al. . |
| 4,429,096 | 1/1984 | Schaefer . |
| 4,855,379 | 8/1989 | Budnik et al. . |
| 4,980,156 | 12/1990 | Raleigh et al. . |
| 4,988,504 | 1/1991 | Zotto et al. . |
| 5,008,103 | 4/1991 | Raleigh et al. . |
| 5,266,715 | 11/1993 | Harisiades et al. ............ 556/420 X |
| 5,312,943 | 5/1994 | Gaglani ...................... 556/420 X |

FOREIGN PATENT DOCUMENTS

| | | |
|---|---|---|
| 0307605 | 3/1989 | European Pat. Off. . |
| 2173005 | 10/1973 | France . |
| 1237247 | 5/1967 | Germany . |
| 7304909 | 10/1973 | Netherlands . |
| 7601202 | 4/1975 | Netherlands . |
| 981812 | 1/1965 | United Kingdom . |
| 1034782 | 7/1966 | United Kingdom . |

Primary Examiner—Paul F. Shaver

[57] ABSTRACT

A novel polysiloxane polyether copolymer useful as a silicone surface active agent is disclosed having improved polyether versatility.

15 Claims, No Drawings

SILICONE POLYETHER SURFACTANTS SYNTHESIZED USING CARBAMATE LINKAGE

This is a divisional of application Ser. No. 07/934,052 filed on Aug. 21, 1992, now abandoned.

The present invention relates to silicone surfactants. More particularly, the present invention relates to silicone polyether surfactants. Most particularly, the present invention relates to silicone surfactants having pendant polyether groups attached to the siloxane backbone by an alkenyl-substituted isocyanato coupling agent.

BACKGROUND OF THE PRESENT INVENTION

The use of polysiloxane surface active agents containing radial organic polyether groups to stabilize silicone emulsions is well known in the art. U.S. Pat. No. 4,265,878 uses a polysiloxane surface active agent to stabilize antiperspirant stick compositions. U.S. Pat. No. 4,218,250 uses such a polysiloxane surface active agent to stabilize polish formulations. U.S. Pat. No. 4,268,499 uses these surface active agents to stabilize antiperspirant emulsion compositions. Further, U.S. Pat. No. 4,311,695 uses polysiloxane polyether surface active agents in personal care creams and the like.

Also, mention is made of U.S. Pat. No. 4,980,156 which describes improved antiperspirant compositions comprising an emulsion of an aqueous astringent in a volatile silicone fluid; U.S. Pat. No. 4,988,504 which discloses silicone polyether copolymers having high molecular weight; and U.S. Pat. No. 5,008,103 which discloses improved silicone surfactants.

Polysiloxane surface active agents are generally referred to a polysiloxane-polyoxyalkylene copolymers. However, their use to date as stabilizers for all types of silicone emulsions has not always been completely satisfactory because the variables affecting their functions are not well understood.

SUMMARY OF THE PRESENT INVENTION

It is an object of the present invention to produce novel polysiloxanes containing organic polyether groups.

It is another object of the present invention to provide a polysiloxane surfactant which is useful as an emulsifier in water-in-oil emulsions.

It is another object of the present invention to provide a polysiloxane surfactant which provides polyether latitude.

It is still another object of the present invention to provide a surfactant which can be either water-soluble or oil-soluble by varying the siloxane backbone and/or the type of pendant ether group.

To these ends, according to the present invention there is provided a novel polysiloxane polymer selected from those of the following formulae: $TD_xM'_3$; $TD_xD'_yM'_3$; $TD'_yM'_3$; $TD_xD'_yM_3$; $TD'_yM_3$; $T'D_xM'_3$; $T'D_xD'_yM'_3$; $T'D'_yM'_3$; $T'D'_yM_3$; $T'D_xD'_yM_3$; $T'D'M_3$; $T'D_xM_3$; $M'D_xD'_yM'$; $M'D_xM'$; $MD'_yM$; $MD_xD'_yM$, $M'D'_yM'$; $M'Q$; $(D')_z$ or mixtures of any of the foregoing; wherein M represents $R_3SiO_{1/2}$; D represents $R_2SiO_{2/2}$; T represents $RSiO_{3/2}$; Q represents $SiO_{4/2}$; M' represents $R_2R^1SiO_{1/2}$; D represents $RR^1SiO_{2/2}$; T' represents $R^1SiO_{3/2}$; each R independently represents a saturated or unsaturated monovalent hydrocarbon; $R^1$ represents an alkyl poly(oxyalkylene) group; x is greater than about 1; y is greater than about 1 and z ranges from 3 to about 12.

Preferably the polysiloxane polymer of the present invention is of the general formula $MD_xD'_yM$ wherein M represents $R_3SiO_{1/2}$; D represents $R_2SiO_{2/2}$; D' represents $RR^1SiO_{2/2}$, each R represents a saturated or unsaturated monovalent hydrocarbon of from 1 to 30 carbon atoms, $R^1$ represents an alkyl(polyoxyalkylene) group; x is greater than about 1 and y is greater than about 1.

Also according to the present invention there is provided a method for preparing the polysiloxane copolymers of the present invention comprising the steps of: (a) reacting an alkenylarylalkylisocyanate with a hydroxy endcapped poly(oxyalkylene) to produce an alkyl(polyoxyalkylene)carbamylalkylarylalkenyl compound; (b) reacting the alkyl(polyoxyalkylene)carbamylalkylarylalkenyl compound with a siloxane hydride fluid selected from those of the general formulae: $TD_xM^H_3$; $TD_xD^H_yM^H_3$; $TD^H_yM^H_3$; $TD_xD^H_yM_3$; $TD^H_yM_3$; $T^HD_xM^H_3$; $T^HD_x D^H_yM^H_3$; $T^HD^H_yM^H_3$; $T^HD^H_yM_3$; $T^HD_xD^H_yM_3$; $T^HD^HM_3$; $T^HD_xM_3$; $M^HD_xD^H_yM^H$; $M^HD_xM^H$; $MD^H_yM$; $MD_xD^H_yM$, $M^HD^H_yM^H$; $M^HQ$; $(D^H)_z$ wherein $M^H$ represents a dialkyl hydrogen siloxy of the formula $R_2HSiO_{1/2}$; $D^H$ represents an alkyl hydrogen siloxy of the formula $RHSiO_{2/2}$; $T^H$ represents an hydrogen siloxy of the formula $HSiO_{3/2}$, and wherein M, D, T, Q, R, x, y and z are as defined above to produce the polysiloxane copolymers of the present invention.

In preferred embodiments of the present invention, the siloxane hydride fluid is of the formula $MD_xD^H_yM$ wherein $D^H$ represents an alkyl hydrogen siloxy of the formula $RHSiO_{2/2}$, and wherein M, D, R, x and y are as defined above.

Still further, according to the present invention there are provided antiperspirant formulations employing the polysiloxane copolymer surfactants of the present invention.

DETAILED DESCRIPTION OF THE PRESENT INVENTION

The present invention provides novel polysiloxane polyether copolymers which are useful as silicone surfactants in a wide variety of applications.

The following description of the present invention will be given with reference to a preferred polysiloxane polyether copolymer. However, the description applies equally to all of the polysiloxane polyethers of the present.

Particularly useful polysiloxane polyether copolymers of the present invention are those generally of the formula

$$MD_xD'_yM$$

wherein M is a monofunctional siloxy group of the formula $R_3SiO_{1/2}$; D is a difunctional siloxy group of the formula $R_2SiO_{2/2}$; D' is a difunctional vinylpolyether substituted siloxy group of the formula $R^1RSiO_{2/2}$, x is above about 1, y is above about 1, R represents a saturated or unsaturated monovalent hydrocarbon, and $R^1$ is a monoalkyl poly(oxyalkylene) group which typically comprises an alkenyl(polyoxyalkylene)carbamyl-alkylarylalkyl group.

In preferred embodiments of the present invention R typically contains no more than six carbon atoms and is selected from those such as alkyl radicals, e.g., methyl, ethyl and isopropyl; cycloaliphatic radicals, e.g., cyclopentyl and cyclohexenyl; olefinic radicals, e.g., vinyl and allyl; and the phenyl radical. Most preferably, R represents a methyl group.

X preferably ranges from about 1 to about 1000, more preferably ranges from about 1 to about 100, and most preferably ranges from about 1 to about 50. Y is preferably in the range of from about 1 to about 1000, more preferably from about 1 to about 50 and most preferably from about 1 to about 20. A particularly useful copolymer is where x is 20 and y is 3.

The copolymers of the present invention can be generally prepared by reacting an alkenyl poly(oxyalkylene) compound with a silicon hydride by hydrosilation techniques known to those skilled in the art.

In a preferred embodiment, a vinyl polyether is synthesized from an alkenyl isocyanate and a polyether by a reaction over a tin catalyst. Preferably, the alkenyl isocyanate comprises a 1-(1-isocyanato-1-methylethyl)-3-(1-methylethenyl)-benzene, which is commercially available as TMI from American Cyanamid Company and described in the patent literature. The polyether can comprise any hydroxy or alkoxy endcapped polyoxyalkylene compound, such as a monomethylether poly(oxyethylene glycol) of 550 molecular weight. Such materials are available commercially, such as Carbowax® 550 from UC Chemicals. Other preferred polyethers are poly(oxypropylene) compounds and/or mixtures of poly(oxypropylene) and poly(oxyethylene) compounds, which are available commercially.

Particularly useful polyethers for the practice of the present invention are those having a molecular weight ranging from about 100 to about 5000.

The reaction proceeds readily and exothermally according to known methods over a tin catalyst, such as a stannous carboxylate, including but not limited to stannous acetate and/or stannous octoate. Since both the isocyanate and stannous catalyst react readily with water, it is preferred that the polyether is dried prior to reaction and moisture is substantially excluded from the reaction vessel. The vinyl polyether is then hydrosilated with a hydride siloxane. The hydride siloxane is preferably of the formula $MD_xD^H_yM$ where $D^H$ represents a hydride siloxane of the formula $RHSiO_{2/2}$ where M, D, R, x and y are as defined above. The hydrosilation reaction is well known to those skilled in the art, and generally proceeds in the presence of a platinum complex catalyst. See, e.g. Karstedt, U.S. Pat. No. 3,775,452; Ashby et al., U.S. Pat. No. 4,288,345; Bailey et al., U.S. Pat. No. 3,336,239; Ashby, U.S. Pat. No. 4,421,903; and Lamoreaux, U.S. Pat. No. 3,220,972. Air may also be introduced to the reaction vessel at controlled levels to activate the platinum catalyst.

It is further contemplated that both the alkenyl poly(oxyalkylene) synthesis reaction and the hydrosilation reaction can be effected in the presence of a suitable solvent such as aromatic hydrocarbons. Typically, the solvent comprises toluene. In the case where the solvent is employed, the solvent can be conveniently removed from the reaction mixtures by stripping under vacuum. Neither the tin nor the platinum catalysts need to be removed, so that the product is easily recovered after stripping by filtration such as through a Celite® filter.

The product emulsifiers of the present invention are capped polyethers, exhibit improved polyether versatility, and are hydrolytically stable. The surfactants can be designed to be water-soluble or oil-soluble by varying the siloxane backbone, i.e., the values of x and y, and/or the type of pendant ether group, i.e., polyether versatility. Thay can also be employed as emulsifiers for water-in-oil personal care products.

The product copolymers are particularly useful in formulating antiperspirant compositions. Typically a water-in-oil antiperspirant comprises (a) a discontinuous aqueous phase, (b) a continuous oil phase, (c) the silicone polyether surface active agents of the present invention, and (d) an organic oil-in-water surfactant.

In preferred embodiments the aqueous phase (a) comprises an aqueous solution of an astringent. Examples of well-known astringents include, but are not limited to, aluminum, hafnium and zirconium salts, such as zirconyl hydroxide halides, aluminum zirconium chloride, zirconium-aluminum lactate, basic aluminum halides such as $Al_2(OH)_5Cl$, aluminum bromide and the several water, alcohol or glycine complexes thereof.

The continuous oil phase (b) generally comprises a volatile liquid having a normal boiling point less than 250° C., and is generally selected from siloxane fluids or paraffinic hydrocarbon fluids.

A particularly useful volatile siloxane fluid are methylsiloxane fluids having the average unit formula $(CH_3)_aSiO_{(4-a)/2}$ where a ranges from 0 to 3 and has an average value of from 2 to 3. Preferably, the volatile methylsiloxane fluid consists essentially of dimethylsiloxane units, and optionally, trimethylsiloxane units. Of particular value as the volatile liquid are the cyclic siloxanes of the general formula $((CH_3)_2SiO)_b$, and the linear siloxanes of the general formula $(CH_3)_3SiO((CH_3)_2SiO)_cSi(CH_3)_3$, and their mixtures, wherein b is an integer of from 3 to 6 and c is an integer of from 0 to 4. A highly preferred methylsiloxane fluid is a mixture of said cyclic siloxanes wherein a major portion is tetramer (b=4) or (b=5).

The organic surfactants (d) comprise any cationic, nonionic or anionic organic surfactant suitable for preparing emulsions of the oil-in-water type and having an HLB value of from 8 to 18 inclusive. Examples of oil-in-water type surfactants include polyethoxylated quaternary ammonium salts and polyoxyethylene fatty amines as cationic surfactants, and polyethylene-glycol alkylethers, polyethyleneglycol alkylarylethers, polyethoxylated sorbitan monolaurate, polyethoxylated sorbitan monooleate, polyoxyethylene lanolin derivatives, and polyethoxylated fatty alcohols as nonionic surfactants. Mixtures of cationic and/or nonionic oil-in-water surfactants are also suitable. Other examples of suitable organic surfactants having an HLB value of from 8 to 18 may be found by consulting standard publications such as McCutcheon's "Detergents and Emulsifiers" 1975 North America Edition, MC Publishing Co., Glen Rock, N.J. 1975.

The amounts (a) and (b) that may be present in the compositions of this invention may vary widely and comprise, in total, from about 99.5 to about 91 percent by weight of the total weight of components (a) through (d). The aqueous solution (a) of astringent may comprise from about 89.5 to about 50, preferably from about 80 to about 65 weight percent of components (a) through (d); however, an efficacious anti-perspirant should contain a sweat-reducing amount, preferably from about 10 to about 25 percent by weight, of the astringent agent itself. A preferred embodiment of this invention is a composition comprising from about 80 to about 65 percent by weight of an aqueous solution of astringent which consists of not more than about 50 weight percent astringent. The volatile liquid (b) comprises from about 10 to about 33 weight percent of the total weight of components (a) to (d).

The surfactant mixture, consisting essentially of components (c) and (d), comprises, in total, from about 0.5 to about 9 percent by weight of the total weight of components (a) and (d), with component (c) accounting for from about 0.4 to about 6 weight percent of the total of components (a) to (d).

The antiperspirant compositions of the present invention may further comprise small amounts of non-essential components which are used in the cosmetic art. Examples of such components include colorants; perfumes; viscosity control additives; and non-volatile organopolysiloxanes, such as polydimethylsiloxanes having a viscosity of from 10 to 10,000 centipoise at 25° C.

The antiperspirant compositions of this invention are suitable for use, without further processing, as a lotion, preferably packaged and dispersed as a roll-on-anti-perspirant composition. However, gel, aerosol and pump-spray formulations may also be prepared therefrom, using well-known adjuvants such as alcohols for gel formation and solvents to reduce the viscosity of the formulation to less than 100 centipoise at 25° C. for aerosol and pump-spray use.

The antiperspirant compositions of the present invention may be prepared by mixing the proper portions of the individual components in any order. Mixing may be done using standard emulsifying methods.

It is further contemplated by the present invention that the silicone polyether surfactants are employed in antiperspirant stick formulations. Typically, these antiperspirant stick formulations comprise (A) from about 100 parts by weight of water having an astringent, as described above, dissolved therein; as a discontinuous phase; in about 100 parts by weight of a continuous oil phase comprising: (B) from about 50 to about 75% by weight of a volatile liquid having a normal boiling point less than 250° C., and is generally selected from siloxane fluids or paraffinic hydrocarbon fluids, as describe hereinabove; (C) from about 25 to about 50% by weight of an organic wax; and (D) a polysiloxane polyether copolymer of the present invention.

Suitable organic waxes include mineral waxes, such as paraffin, etc.; vegetable waxes, such as carnauba, flax, candelilla, etc.; microcrystalline waxes; montan waxes; and animal waxes such as bees wax. Chemically these waxes are branched or straight chain hydrocarbons, high molecular weigh fatty acid, high molecular weigh alcohols, or high molecular weigh fatty acid esters. Characteristically waxes have low viscosities just above their melting point. For use herein, the waxes should have a melting point between about 40° C. and 65° C. Such a melting point allows for proper application rates and prevents melting upon storage under ambient conditions. Preferably the organic wax is a mixture of waxes to control the hardness of the stick composition. Thus, a preferred organic wax is a mixture of a waxy ester for hardness, such as methyl hydroxystearate, and a solid alkanol such as stearyl alcohol. Where such a mixture of waxes is used, the organic wax might contain 10 to 50% by weight solid alkanol and 50 to 90% by weight waxy ester. Hardness is also greatly effected by the proportion of organic wax in the stick composition. Preferably, the continuous oil matrix contains about 25 to 40% by weight organic wax.

The antiperspirant stick compositions of the present invention are easily prepared by methods well known in the art. In one embodiment, the cyclic polysiloxane, organic wax and silicone polyether surfactant of the present invention are heated until all components are liquid and then mixed. Generally the components will liquify between about 40° and 70° C. Subsequently, the water solution with active ingredient is warmed and emulsified into the molten wax as is known. The warm emulsion is poured as close to solidification temperature as possible into molds and allowed to cool.

Other surfactants and additives may be included in the stick compositions of the present invention, as is known in the art. For example, talc may be added to the oil phase. Further, other surfactants may be employed in the stick formulations.

DESCRIPTION OF THE PREFERRED EMBODIMENTS

The following examples illustrate the present invention. They are not to be construed to limit the scope of the appended claims in any manner whatsoever.

EXAMPLE 1

500 g of toluene and 739 g of Carbowax® 550 (monomethylether poly(oxyethylene glycol) from UC Chemicals) were azeotroped dry in a suitable vessel. To the mixture was then added 0.1 g of tin acetate catalyst, and the mixture was heated to 100° C. 261 g of TMI (American Cyanamid Company) was fed to the mixture, controlling the exotherm. The TMI isocyanate reaction was monitored by infrared spectroscopy. Upon completion, the reaction mixture was cooled and filtered through Celite® 545. The filtrate is stripped to pot temperature of 130° C. under vacuum to remove the toluene to obtain a vinyl polyether.

EXAMPLE 2

500 g of toluene and 440 g of a methyl hydride siloxane of the formula $MD_{20}D^H_3M$, where M, D and $D^H$ are as defined above (molecular weight 1822), are azeotroped dry. The mixture is heated to 100° C. and 0.6 g of a platinum alcoholate (Lamoreaux, U.S. Pat. No. 3,220,972) is added. 560 g of the vinyl polyether of Example 1 is then added over a 1 hour period at 100° C. The mixture is then cooked for 5 hours at 100° C., and the reaction is checked for completion by infrared spectroscopy to determine the presence of unreacted silicon hydride sites.

Upon completion of the reaction, the mixture is stripped of toluene at pot temperature of 130° C. under 20 mm vacuum. The mixture is held at these conditions for 1 hour, and then cooled to less than 70° C. and vacuum broken. The stripped mixture is filtered through Celite® 545. The product copolymer has a viscosity of 1256 centistokes.

EXAMPLE 3

The emulsifier prepared in Example 2 is employed in a water-in-oil emulsion. First the oil phase is prepare by mixing 17.0 parts by weight of a heavy mineral oil, 3.0 parts by weight of SF-1202 (a cyclomethyl siloxane fluid, General Electric Company), and 2.0 parts by weight of the emulsifier of Example 2.

Second, the aqueous phase is prepared by mixing together 3.0 parts by weight of propylene glycol, 1.0 part by weight of sodium chloride and 74.0 parts by weight of water.

The oil-phase is then added to the aqueous phase with high shear agitation. The emulsion formed is then milled in a Gifford-Wood homogenizer to increase stability. A stable water-in-oil emulsion is thereby prepared with the scope of the appended claims.

The above-mentioned patents are hereby incorporated by reference.

Many variations of the present invention will suggest themselves to those of ordinary skill in the art in light of the above-detailed description. All such obvious modifications are within the full intended scope of the appended claims.

We claim:

1. A silicone polyether of the general formula $MD_xD'_yM$ wherein M represents $R_3SiO_{1/2}$; D represents $R_2SiO_{2/2}$; D' represents $RR^1SiO_{2/2}$, each R represents a saturated or unsaturated or unsaturated monovalent hydrocarbon, $R^1$ represents an alkyl poly(oxyalkylene) carbamylalkyl arylalkyl group or a monomethyl poly(oxyethylene)-carbamylisopropyl aryl methyl ethenyl group; x is greater than about 1 and y is greater than about 1.

2. A silicone polyether as defined in claim 1 wherein $R^1$ represents a monomethyl poly(oxyethylene)carbamylisopropylarylmethylethenyl group.

3. A silicone polyether of the general formula

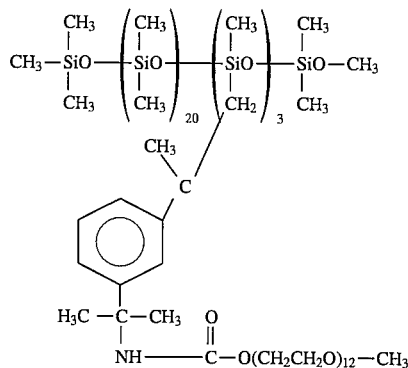

4. A method for preparing a silicone polyether surfactant comprising a polysiloxane copolymer selected from those of the general formulae: $TD_xM'_3$; $TD_xD'_yM'_3$; $TD'_yM'_3$; $TD_xD'_yM_3$; $TD'_yM_3$; $T'D_xM'_3$; $T'D_xD'_yM'_3$; $T'D'_yM'_3$; $T'D'_yM'_3$; $T'D_xD'_yM_3$; $T'D'M_3$; $T'D_xM_3$; $M'D_xD'_yM'$; $M'D_xM'$; $MD'_yM$; $MD_xD'_yM$, $M'D'_yM'$; $M'Q$; $(D')_z$ or mixtures of any of the foregoing; wherein M represents $R_3SiO_{2/2}$; D represents $R_2SiO_{2/2}$; T represents $RSiO_{3/2}$; Q represents $SiO_{4/2}$; M' represents $R_2R^1SiO_{1/2}$; D represents $RR^1SiO_{2/2}$; T' represents $R^1SiO_{3/2}$; each R independently represents a saturated or unsaturated monovalent hydrocarbon; $R^1$ represents an alkyl poly(oxyalkylene) group; x is greater than about 1; y is greater than about 1 and z ranges from 4 to about 12;

comprising the steps of:

(a) reacting an alkenylarylalkylisocyanate with a hydroxy endcapped polyoxyalkylene to produce an alkyl(polyoxyalkylene)carbamylalkylarylalkenyl compound;

(b) reacting the alkyl(polyoxyalkylene)carbamylalkylarylalkenyl compound with a siloxane hydride fluid selected from those of the general formulae: $TD_xM^H_3$; $TD_xD^{H}_yM^H_3$; $TD^H_yM^H_3$; $TD_xD^H_yM_3$; $TD^H_yM_3$; $T^HD_xM^H_3$; $T^HD_xD^H_yM^H_3$; $T^HD^H_yM^H_3$; $T^HD^H_yM^H_3$; $T^HD_xD^H_yM_3$; $T^HD^HM_3$; $T^HD_xM_3$; $M^HD_xD^H_yM^H$; $M^HD_xM^H$; $MD^H_yM$; $MD_xD^H_yM$, $M^HD^H_yM^H$; $M^HQ$; $(D^H)_z$ wherein $M^H$ represents a dialkyl hydrogen siloxy of the formula $R_2HSiO_{1/2}$; $D^H$ represents an alkyl hydrogen siloxy of the formula $RHSiO_{2/2}$; $T^H$ represents an hydrogen siloxy of the formula $HSiO_{3/2}$, and wherein M, D, T, Q, R, x, y and z are as defined above to produce said polysiloxane copolymer.

5. A method as defined in claim 4 wherein said siloxane hydride fluid is of the formula $MD_xD^H_yM$ and said polysiloxane copolymer is of the general formula $MD_xD'_yM$; wherein M, D, D', $D^H$, x and y are as defined above.

6. A method as defined in claim 5 wherein R represents methyl.

7. A method as defined in claim 5 wherein $R^1$ represents a monomethyl poly(oxyethylene)carbamylisopropylcumenyl group.

8. A method as defined in claim 5 wherein x ranges from about 1 to about 1000.

9. A method as defined in claim 5 wherein x ranges from about 1 to about 50.

10. A method as defined in claim 5 wherein y ranges from about 1 to about 1000.

11. A method as defined in claim 5 wherein y ranges from about 1 to about 10.

12. A method as defined in claim 5 wherein said alkenylarylalkylisocyanate comprises 1-(1-isocyanato-1-methylethyl)-3-(1-methylethenyl)-benzene.

13. A method as defined in claim 5 wherein said hydroxy endcapped polyoxyalkylene comprises monomethyl poly(oxyethylene)hydroxyl.

14. A method as defined in claim 5 wherein step (a) proceeds under substantially anhydrous conditions and in the presence of a stannous carboxylate catalyst.

15. A method as defined in claim 5 wherein step (b) is a hydrosilation reaction in the presence of a platinum catalyst.

* * * * *